United States Patent [19]

Ker

[11] Patent Number: 4,980,044

[45] Date of Patent: Dec. 25, 1990

[54] OXYGEN SENSOR HAVING A FLAT PLATE ELEMENT AND HEATER

[75] Inventor: Eric L. Ker, Grand Blanc, Mich.

[73] Assignee: General Motors Corporation, Detroit, Mich.

[21] Appl. No.: 331,482

[22] Filed: Mar. 31, 1989

[51] Int. Cl.⁵ .......................................... G01N 27/406
[52] U.S. Cl. ..................................... 204/426; 204/424
[58] Field of Search .............................. 204/421–429

[56] References Cited

U.S. PATENT DOCUMENTS

| | | | |
|---|---|---|---|
| 3,216,911 | 11/1965 | Kronenberg | 204/427 |
| 4,076,608 | 2/1978 | Fujishiro et al. | 204/427 |
| 4,193,965 | 3/1980 | Cullingford | 204/426 |
| 4,282,080 | 8/1981 | Muller et al. | 204/195 S |
| 4,300,990 | 11/1981 | Maurer | 204/195 S |
| 4,505,807 | 3/1985 | Yamada | 204/426 |
| 4,797,194 | 1/1989 | Mase et al. | 204/425 |

Primary Examiner—T. Tung
Attorney, Agent, or Firm—Domenica N. S. Hartman

[57] ABSTRACT

An oxygen sensing device is proposed which has a unique sensing element. The sensing element is substantially flat and comprises a solid electrolyte material, preferably yttria stabilized zirconia. The sensing element has a measuring electrode which contacts the external gas to be measured and a reference electrode which contacts a known concentration of gas. A positive resistance heater element may also be provided on the solid electrolyte body of the sensing element.

A unique feature of the flat sensing element is that the sides of the solid electrolyte body converge at an apex located between the two ends of the body, so that the width of the body is greatest at the apex and tapers from the apex toward the two ends. The tapers facilitate secure and rigid retention of the sensing element within a housing. The sensing element is fixtured within the housing by packing the sensing element in a pressure media between two bushings located on either side of the apex, and crimping the two bushings. Fixturing the solid electrolyte body within the housing in this manner advantageously results in the crimping force being distributed over the surface of the ceramic sensing element and the ceramic sensing element being held in compression.

5 Claims, 3 Drawing Sheets

OXYGEN SENSOR HAVING A FLAT PLATE ELEMENT AND HEATER

The present invention generally relates to an electrochemical type solid electrolyte oxygen sensor suitable for detecting oxygen concentrations in automotive exhaust emitted from an internal combustion engine. More specifically, this invention relates to an oxygen sensor of this type which has a unique flat plate, solid electrolyte sensing element, which preferably also includes means for self heating itself to a predetermined temperature.

BACKGROUND OF THE INVENTION

Gas sensors are employed in a variety of applications requiring qualitative and quantitative gaseous determinations. In the automotive industry, it is well known that the oxygen concentration in the automobile exhaust has a direct relationship to the engine air-to-fuel ratio. Oxygen gas sensors are employed within the automobile internal combustion control system to provide accurate exhaust gas oxygen concentration measurements for determination of optimum combustion conditions, maximization of efficient fuel usage, and management of exhaust emissions.

Generally, the electrochemical type of oxygen sensor employed in automotive applications utilizes a thimble shaped electrochemical galvanic cell to determine, or sense, the relative amounts of oxygen present in the exhaust stream, an example being U.S. Pat. No. 3,844,920 to Burgett et al. This type of oxygen sensor is generally known and used throughout the automotive industry, and comprises an ionically conductive solid electrolyte material, typically yttria stabilized zirconia, a porous electrode coating on the exterior exposed to the exhaust or measuring gas and a porous electrode coating on the interior exposed to a known concentration of reference gas.

The gas concentration gradient across the solid electrolyte produces a galvanic potential which is related to the differential of the partial pressures of the gas at the two electrodes by the Nernst equation: $E = AT \ln[P_1/P_2]$, where E is the galvanic voltage, T is the absolute temperature of the gas, $P_1/P_2$ is the ratio of the partial pressures of the reference gas at the two electrodes, and $A = R/4F$, where R is the universal gas constant and F is the Faraday constant. Thus, the oxygen sensor senses the oxygen concentration in the exhaust gas by measuring this galvanic output voltage.

However, it is desirable to first heat the solid electrolyte of such a sensor to an elevated temperature. This enables the sensor to immediately obtain an appreciable output voltage in response to the difference in the oxygen concentrations between the reference and measuring electrodes. The induced galvanic potential between electrodes and corresponding output voltage are not stable until the solid electrolyte has been heated to a given temperature. In operation, the combustion gases heat the solid electrolyte of the oxygen sensor to an operating temperature sufficient to effect galvanic stability. Therefore, effective sensor operation is delayed until the combustion gases heat the sensor to a suitable temperature.

Lastly, if the sensor is placed too far downstream in the exhaust pipe of an engine, especially a highly efficient engine, the sensor may not be heated to a high enough temperature during engine idle to meet sensor specifications. During these conditions, the internal combustion engine control system operates open loop, i.e., the control system does not sense the controlled parameter, air-to-fuel ratio, in order to control that parameter. It is known that a large percentage of the total emissions produced during short periods of operation are produced during this period, engine warm up. Therefore, in some applications, emissions control during engine warm up would be improved with an oxygen sensor which had means for rapidly heating itself to a predetermined temperature, regardless of the temperature of the surrounding environment. Also desirable about an oxygen sensor which can heat itself is that it may be placed anywhere in the exhaust pipe, even at the cooler exit end, since the solid electrolyte of the sensor is not dependent on the heat of the combustion gases for heating itself.

Many heated oxygen sensors have been previously proposed in the art. These prior heated oxygen sensors generally comprise an elongated ceramic heater which positively heats the solid electrolyte body of the sensor. The heater element is typically inserted into an elongated cylindrical hole formed in the conventional thimble shaped solid electrolyte body.

Although these prior types of heated and unheated oxygen sensors have performed satisfactorily during operation, it is desirable to develop a sensing element which is not thimble shaped. A shortcoming of the oxygen sensors having the thimble shaped elements are that they are accordingly difficult to manufacture and assemble.

It is therefore desirable to provide a sensing element which utilizes a flat plate ceramic substrate and which utilizes standard ceramic processing techniques. In addition, it is also desirable that such a sensing element be capable of rapidly heating itself to a predetermined temperature. Further, for automotive applications particularly, the heated oxygen sensing element should be rugged, reliable, and readily manufacturable at a low cost.

SUMMARY OF THE INVENTION

It is an object of the present invention to provide an improved solid electrolyte sensing element for an electrochemical oxygen sensor.

It is a further object of this invention that such improved sensing element be formed from a flat plate ceramic substrate.

It is still a further object of this invention that such improved sensing element have means for rapidly self heating itself to a predetermined temperature.

In accordance with the preferred embodiment of this invention, these and other objects and advantages are accomplished as follows.

According to the present invention, there is provided a unique solid electrolyte oxygen sensing element suitable for detecting oxygen concentrations in automotive exhaust emitted from an internal combustion engine.

The preferred sensing element is substantially flat and comprises a solid electrolyte material, preferably yttria stabilized zirconia. The sensing element has a measuring electrode which contacts the external gas to be measured and a reference electrode which contacts a known concentration of gas. A positive resistance heater element is also preferably provided on the solid electrolyte body of the sensing element.

A unique feature of the flat plate ceramic sensing element is that the sides of the sensing element converge at an apex located between the two ends of the element, so that the width of the element is greatest at the apex and tapers from the apex toward the two ends. The tapers facilitate secure and rigid retention of the sensing element within the housing. The sensing element is rigidly held within the housing by packing the sensing element in a pressure media, such as talc, and crimping two bushings which are located on either side of the apex. Rigidly holding the sensing element within the housing in this manner advantageously results in the crimping force being spread over the surface of the sensing element and not concentrated at the apex, and the sensing element being held in compression, thereby promoting longer life of the sensing element.

Other objects and advantages of this invention will be better appreciated from the following detailed description.

DETAILED DESCRIPTION OF THE INVENTION

This invention provides a heated, solid electrolyte sensing element for use in an electrochemical oxygen sensing device which is suitable for detecting oxygen partial pressures of exhaust gases emitted from an internal combustion engine.

Generally, the preferred sensing element is formed from a substantially flat body of solid electrolyte material, preferably yttria stabilized zirconia, and has a measuring electrode which contacts the external gas to be measured and a reference electrode which contacts a known concentration of gas. A positive resistance heater element is also provided on the sensing element.

A unique feature of this invention is the shape of the sensing element. The sides of the solid electrolyte body converge at an apex located between the two ends of the body. Therefore, the width of the body is greatest at this apex and tapers from the apex toward the two ends of the body. The tapers facilitate secure and rigid retention of the solid electrolyte body within a housing. The sensing element is rigidly held within the housing by packing the sensing element in a pressure media, such as talc, and crimping two bushings located on either side of the apex. With this invention, the sensing element is held in compression within the housing and the crimping force is spread evenly over the element, not concentrated at the apex, which is advantageous since it promotes durability and a longer life for the ceramic solid electrolyte body.

Figure 1:
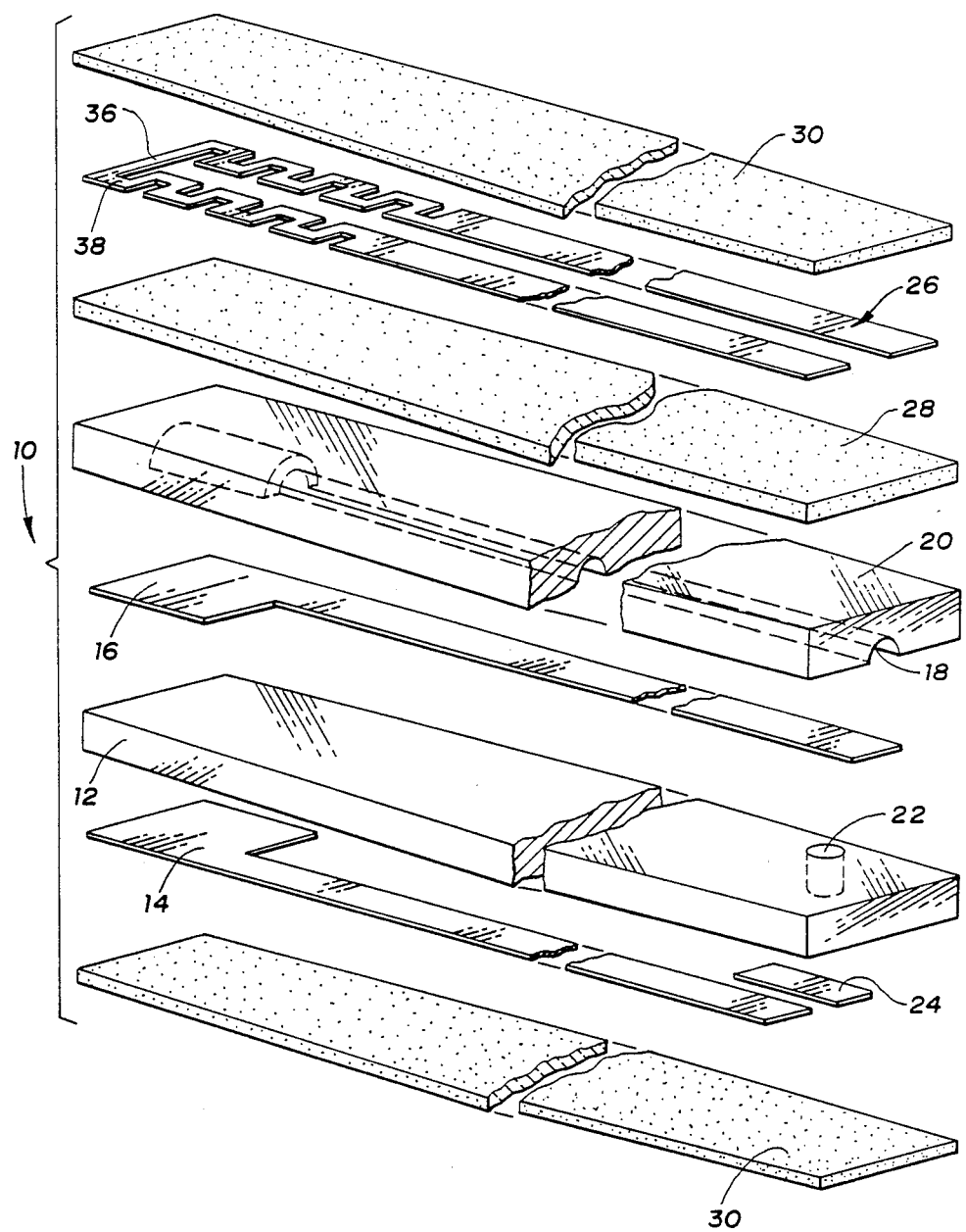
FIG. 1 is an exploded view of the components of a flat plate sensing element in accordance with a preferred embodiment of this invention.

FIG. 1 is an exploded illustration of the components of the preferred flat plate sensing element 10. The sensing element 10 comprises a first solid electrolyte body 12, preferably yttria stabilized zirconia. That solid electrolyte body 12 has a measuring electrode 14 and a reference electrode 16. Both electrodes 14 and 16 are preferably comprised of porous platinum however other suitable materials which are electrically conductive and porous so as to permit measurement of the oxygen partial pressure in the exhaust gas may also be used. The measuring electrode 14 contacts the external gas to be measured, such as the automotive exhaust gases.

The reference electrode 16 is disposed so as to be gas tight from the external gases and instead contacts a known concentration of reference gas. The known concentration of reference gas is provided by a chamber 18, or air channel, in an overlaying body 20 of material which seals the reference electrode 16. Preferably, the shape of the reference chamber 20 substantially matches the shape of the reference electrode 16 so as to allow maximum movement of the reference gas and optimum contact between the reference electrode 16 and reference gas. However, this is not necessary, so long as the reference gas contacts the reference electrode 16 at some region.

A via hole 22 and contact pad 24 are provided on the solid electrolyte body 12 to permit electrical connection of the reference electrode 16 to external measuring electronics (not shown). The via hole 22 and contact pad 24 are comprised of an electrically conductive material, such as the porous platinum used to form the reference electrode 16.

The overlaying body 20 of material preferably comprises the same material as the solid electrolyte body 12, i.e., preferably yttria stabilized zirconia. Although other suitable materials may be used, it is desirable to use the same material for the overlaying body 20 as the solid electrolyte body 12 for ease in construction, and for minimization of stress.

A positive resistance heater element 26 is preferably provided on the sensing element 10. The heater element 26 is formed from preferably platinum, however other suitable materials such as tungsten may also be used. The platinum is patterned and deposited onto a layer of dielectric material 28, preferably aluminum oxide Al$_2$O$_3$. The dielectric material 28 is deposited onto the overlaying body of material 20 having the air channel 18. Although the heater element 26 could be disposed directly on the overlaying body 20 having the air channel 18, the intervening dielectric layer 28 is preferred to prevent any ionic or electrical conduction between the porous platinum reference electrode 16 and the platinum heater element 26 through the ionically and electrically conductive solid electrolyte overlaying body 20.

The heater element 26 is characterized by a positive coefficient of resistance. Therefore, the heater element 26 generates less heat as its temperature rises. This is desirable since the heater element 26 is primarily used only when the exhaust gases are at low temperature. Accordingly the heater element 26 becomes unnecessary when the exhaust gases are at an elevated temperature.

Although the preferred embodiment of this invention includes a heater element 26, it is foreseeable that a heater may not be desired. If so, the sensing element 10 would be constructed as described above, except that the heater element 26 and dielectric layer 28 would be omitted. With this alternative unheated embodiment, the sensing element would sense the gas to be measured only after it has been heated to a predetermined temperature, such as by being heated to temperature by the exhaust gases.

In addition, a protective layer 30 of material, such as spinel, may be deposited over the heater element 26 and measuring electrode 14. Spinel is the preferred material since it is porous and compatible with the underlying materials. The spinel layer 30 protects the underlying elements yet permits diffusion of the gases through to the underlying measuring electrode 14. Although spinel is preferred, other suitable materials which provide protection and porosity may also be used.

An inventive feature of this invention is that the sensing element 10 is tapered. As clearly shown in FIGS. 2 and 3, the sides of the sensing element 10 are tapered outward and converge at an apex 32 on both sides of the solid electrolyte body 12. The apex 32 is located between the top and bottom ends, 34 and 36 respectively, of the sensing element 10. The width of the sensing element 10 is greatest at the apex 32. The tapered shape of the sensing element 10 permits the sensing element 10 to be easily held and self-locating within an oxygen sensor assembly.

It is preferred that the taper angle $\phi$ be greater than about 165 degrees, as measured from the inside of the apex 32 between the two converging sides of the sensing element 10. This permits the use of conventional bushings, an example shown in FIG. 4. The taper angle $\phi$ may be less than 165 degrees, i.e., the apex 32 may be more pointed, however, this requires special bushings. Preferably, the taper angle $\phi$ is between approximately 175 to 179 degrees. This permits the use of a conventional bushing and reduces the stress concentration at a sharp apex which thereby reduces the probability of delamination or cracking at the apex 32. Even more preferably, the taper angle $\phi$ should be about 179 degrees, as this optimizes the competing concerns of structural integrity and stress concentration, as well as manufacturability.

Figure 2:
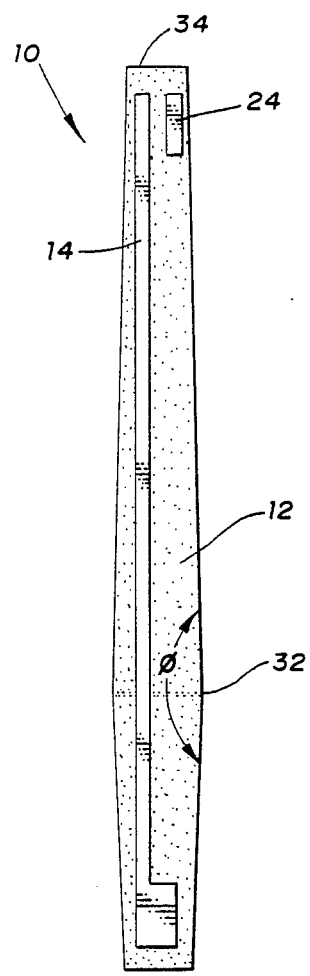
FIG. 2 is a plan view of a first side of a preferred flat plate sensing element as shown in FIG. 1 and illustrates the preferred tapered sides of the element.

FIG. 2 is a plan view of the sensing element 10. The protective outer layer of spinel is not shown so that the position of the measuring electrode 14 may be seen. The measuring electrode 14 contacts the external gas to be measured. The contact pad 24 is also illustrated. The contact pad 24 provides electrical connection between (1) the reference electrode (not shown) which is provided on the opposite face of the solid electrolyte body 12 from the measuring electrode 14, and (2) the external measuring equipment (not shown), by means of the electrically conductive via hole 22 through the solid electrolyte body 12. The contact pad 24 and via hole 22 are not necessary, so long as electrical connection may be made by other means to the reference electrode 16.

Figure 3:
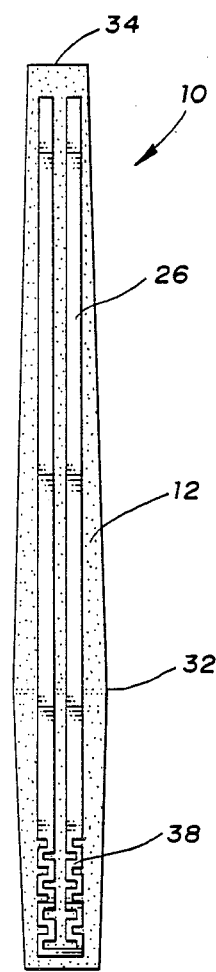
FIG. 3 is a plan view of a second side of a preferred flat plate sensing element as shown in FIG. 1 and also illustrates the preferred tapered sides of the element.

FIG. 3 illustrates a plan view of the opposite face of the sensing element 10. Again, the protective outer layer of spinel is not shown so that the position of the heater element 26 may be shown. The heater element 26 comprises thick film platinum, tungsten or other suitable material. The heater element 26 is patterned so as to be convoluted 38 at its bottom end 36, where the exhaust gases primarily flow. This design is preferred because it provides substantially more heat to that region of the solid electrolyte body 12 which contacts the exhaust gases, and thereby heats up that region more quickly for more immediate gas concentration measurements.

Figure 4:
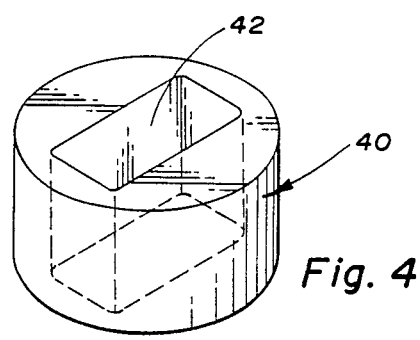
FIG. 4 is a perspective view of a bushing for fixturing the preferred sensing element shown in FIG. 1.

An exemplary bushing 40 is illustrated in FIG. 4. The bushing 40 has an inner slot 42 which is slightly less than the outer perimeter of the apex 32 of the sensing element 10. This design results in a friction interference fit between the sensing element 10 and the bushing 40 at regions away from the apex 32 of the sensing element 10. The preferred material for the bushing 40 is alumina, primarily because of its coefficient of thermal expansion. However other suitable materials with coefficients of expansion comparable to the sensing element 10 may also be used, such as zirconia.

Figure 5:
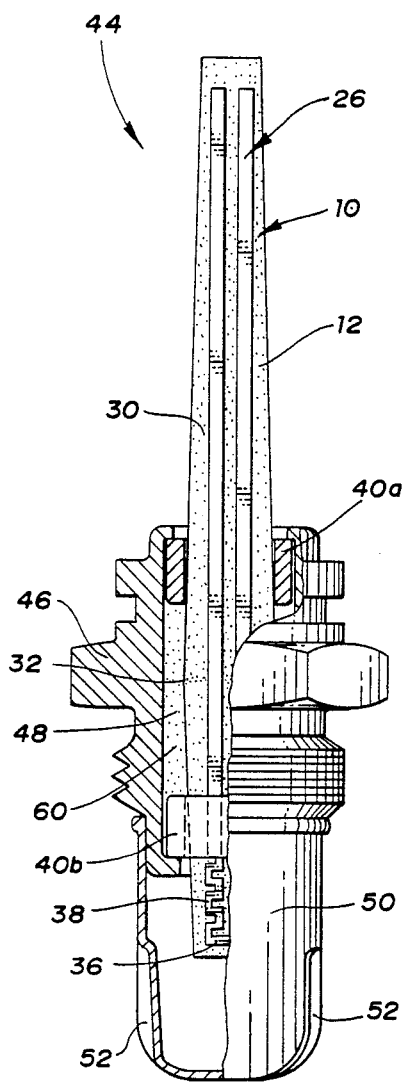
FIG. 5 is a cross-sectional view of the preferred sensing element subassembly wherein the sensing element is rigidly and securely fixtured within its housing by means of two bushings, an example of the bushing shown in FIG. 4.

FIG. 5 illustrates the sensing element subassembly 44 wherein the sensing element 10 is securely and rigidly fixtured with two bushings 40a and 40b within the housing 46. The sensing element 10 is packed in the metal housing 46 with the two bushings 40a and 40b on each side of the apex 32 of the sensing element 10. A pressure media 60 is compacted around the sensing element 10 in the metal housing 46 in that region 48 between the two bushings 40a and 40b. The preferred material for the pressure media 60 is talc because of its extremely low coefficient of thermal expansion and physical properties. However other suitable materials such as ceramic or glass powders may also be used as the pressure media 60.

Another inventive feature of this invention is the manner in which the sensing element 10 is rigidly secured within the housing 46. The sensing element 10 is self centering within the housing 46 because of its design and the placement of the bushings 40a and 40b. A crimping force is applied from both bushings 40a and 40b to the sensing element 10 through the pressure media 60. This design results in a distribution of force spread over the element 10 surface, instead of concentrated at the apex 32 or any other region. Further, the design results in the ceramic sensing element 10 being held in compression, which is significantly more desirable when working with ceramic materials and which results in longer life of the ceramic sensing element 10. With this design, the sensing element 10 is securedly and rigidly fixtured inside the metal housing 46 and does not move during thermal cycling, vibration or operation of the automobile.

The crimping force, or compressive force, required to hold the sensing element 10 is preferably about 600 psi. The force should not exceed the stress yield point of the solid electrolyte substrate 12 of the sensing element 10, i.e., the yttria stabilized zirconia solid electrolyte body 12. Therefore, it is foreseeable that the force could vary between about 100 to about 3000 psi without detriment to the sensing element 10.

The housing 46 supports the sensing element 10 so that the measuring electrode 14 of the sensing element 10 contacts the external gases to be measured, while maintaining the reference electrode 16 gas tight to these external gases. The sensing element 10 is mounted so as to resemble a finger like projection into the flow of the exhaust gases.

A perforated, protective metal shield 50 is also shown in FIG. 5. This shield 50 protects the sensing element 10, and has perforations 52 so as to allow uninterrupted flow of the exhaust gases around the sensing element 10. The shield 50 and housing 46 are exposed to the harsh exhaust gases and therefore should be formed from a suitable material such as a stainless steel.

Figure 6:
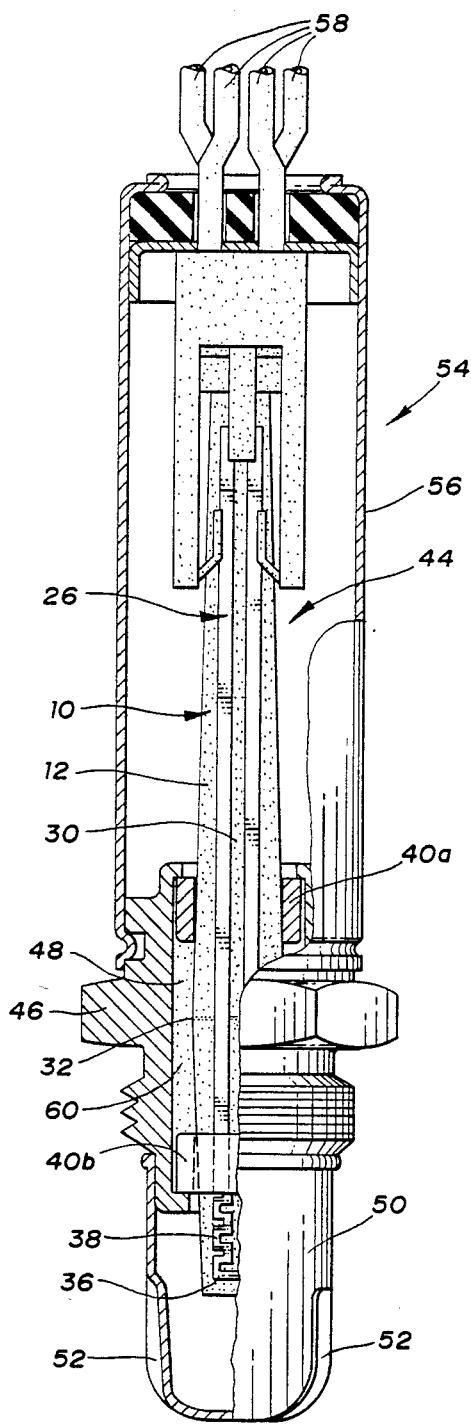
FIG. 6 is a cross-sectional view of a preferred oxygen sensor comprising the preferred sensing element.

FIG. 6 depicts the entire oxygen sensor assembly 54 wherein the upper protective shield 56 and electrical connections 58 are installed with the sensing element subassembly 44. The upper shield 56 provides additional protection to the upper portion of the sensing element 10. The electrical connections 58 communicate the electrical signals generated by the sensing element 10 to electrical measuring equipment (not shown).

While our invention has been described in terms of a preferred embodiment, it is apparent that other forms could be adopted by one skilled in the art, such as by the use of different materials, or the use of a more tapered sensing element with appropriately formed bushings and pressure media. Accordingly, the scope of our invention is to be limited only by the following claims.

The embodiments of the invention in which an exclusive property or privilege is claimed are defined as follows:

1. An oxygen sensing device comprising:
    a substantially flat solid electrolyte body having a measuring electrode and a reference electrode;
    said solid electrolyte body having a first and second end, and sides which each converge from said first and second ends towards an apex located between said first and second ends so that the width of said body is greatest at said apexes and tapers from said apexes toward said first and second ends, and so that said solid electrolyte body is characterized by having a substantially hexagonal cross-section; and
    a housing, said housing supports said solid electrolyte body so that said measuring electrode of said solid electrolyte body contacts the external gas to be measured and so that said reference electrode of said solid electrolyte body is gas tight to the external gas to be measured;
    wherein said solid electrolyte body is securely and rigidly maintained within said housing by two bushings, a first bushing being located between said apexes and said first end of said solid electrolyte body and said second bushing being located between said apexes and said second end of said solid electrolyte body.

2. An oxygen sensing device as recited in claim 1 wherein said solid electrolyte body further comprises a positive resistance heater.

3. An oxygen sensing device comprising:
    a substantially flat solid electrolyte body having a porous platinum measuring electrode and a porous platinum reference electrode, and a positive resistance heater;
    said solid electrolyte body having a first and second end, and sides which each converge from said first and second ends towards an apex located between said first and second ends so that the width of said body is greatest at said apexes and tapers from said apexes toward said first and second ends, and so that said solid electrolyte body is characterized by having a substantially hexagonal cross-section; and
    a housing, said housing supports said solid electrolyte body so that said measuring electrode of said solid electrolyte body contacts the external gas to be measured and so that said reference electrode of said solid electrolyte body is gas tight to the external gas to be measured, and so that said positive resistance heater is located primarily in that region where the external gases are contacted;
    wherein said solid electrolyte body is securely and rigidly maintained within said housing by two bushings, a first bushing being located between said apexes and said first end of said solid electrolyte body and said second bushing being located between said apexes and said second end of said solid electrolyte body.

4. A sensing element suitable for use in an oxygen sensing device, comprising:
    a substantially flat solid electrolyte body having a measuring electrode and a reference electrode;
    said solid electrolyte body having a first and second end, and sides which each converge from said first and second ends towards an apex located between said first and second ends to that the width of said body is greatest at said apexes and tapers from said apexes toward said first and second ends, and so that said solid electrolyte body is characterized by having a substantially hexagonal cross-section.

5. A sensing element suitable for use in an oxygen sensing device, comprising:
    a substantially flat solid electrolyte body having a porous platinum measuring electrode and a porous platinum reference electrode, and a positive resistance heater disposed primarily along the length of said body;
    said solid electrolyte body having a first and second end, and sides which each converge from said first and second ends towards an apex located between said first and second ends so that the width of said body is greatest at said apexes and tapers from said apexes toward said first and second ends, and so that said electrolyte body is characterized by having a substantially hexagonal cross-section.

* * * * *